United States Patent [19]
Arpadi et al.

[11] Patent Number: 5,840,042
[45] Date of Patent: Nov. 24, 1998

[54] METHOD OF PREDICTING BODY COMPOSITION IN PREPUBERTAL CHILDREN INFECTED WITH HUMAN IMMUNODENFICIENCY VIRUS

[75] Inventors: Stephen M. Arpadi; Mary Horlick, both of New York; Donald P. Kotler, New Rochelle, all of N.Y.; Richard N. Pierson, Englewood, N.J.; John Thornton, Mahopac, N.Y.; Jack Wang, Edgewater, N.J.

[73] Assignee: St. Luke's-Roosevelt Hospital, New York, N.Y.

[21] Appl. No.: 857,390

[22] Filed: May 16, 1997

[51] Int. Cl.$^6$ ..................................................... A61B 5/05
[52] U.S. Cl. ............................. 600/547; 600/587; 73/433
[58] Field of Search ................................... 600/547, 506, 600/587; 73/433

[56] References Cited

U.S. PATENT DOCUMENTS

| | | | |
|---|---|---|---|
| 5,597,797 | 1/1997 | Clark | 514/12 |
| 5,628,328 | 5/1997 | Nissen et al. | 600/587 |
| 5,720,296 | 2/1998 | Cha | 600/547 |

OTHER PUBLICATIONS

S.M. Arpadi et al., "Accuracy of Body Composition Measurements by Bioimpedance Analysis in Children Infected with HIV–1," XI International Conference on AIDs, Vancouver, Canada, Jul. 7–12, 1996.

S.M. Arpadi et al., "Application on Bioimpedance Analysis for Estimating Body Composition in Prepubertal Children Infected with Human Immunodeficiency Virus Type 1," 129 *J. Pediatr.*, pp. 755–757 (1996).

D.B. Check et al., "Body Water, Height, and Weight During Growth in Normal Children," 112 *Amer. J. Dis. Child.*, pp. 312–317 (1966).

T.L. Miller, "Nutritional Assessment and its Clinical Application in Children Infected with the Human Immunodeficiency Virus," 129 *J. Pediatr.*, pp. 633–636 (1996).

R.F. Kushner et al., "Estimation of Total Body Water by Bioelectrical Impedance Analysis," 44 *Am. J. Clin. Nutr.*, pp. 417–242 (1986).

C.R. Fjeld et al., "Total Body Water Measured by $^{18}$O Dilution and Bioelectrical Impedance in Well and Malnourished Children," 27 *Pediatric Research*, pp. 98–102 (1990).

P.S.W. Davies et al., "The Prediction of Total Body Water Using Bioelectrial Impedance in Children and Adolescents," 15 *Ann. Human Biology*, pp. 237–240 (1988).

L.B. Houtkooper et al., "Bioelectrical Impedance Estimation of Fat–Free Body Mass in Children and Youth: A Cross–Validation Study," 72 *J. Appl. Physiol.*, pp. 366–373 (1992).

L. Cordain et al., L"Body Composition Determination in Children Using Bioelectrical Impedance," 52 *Growth Development & Aging*, pp. 37–40 (1988).

L.C. Danford et al., "Comparison of Two Bioelectrical Impedance Analysis Models for Total Body Water Measurement in Children," 19 *Ann. Hum. Biology*, pp. 603–607 (1992).

P. Deurenberg et al., "Assessment of Body Composition by Bioelectrical Impedance in Children and Young Adults is Strongly Aged–Dependent," 44 *European J. of Clin. Nutr.*, pp. 261–268 (1989).

R.E. McKinney Jr. et al., "Growth as a Prognostic Indicator in Children with Human Immunodificiency Virus Infection Treated with Zidovudine," 125 *J. Pediatrics*, pp. 728–733 (1994).

J.W. Gregory et al., "Body Water Measurement in Growth Disorders: A comparison of Bioelectrical Impedance and Skinfold Thickness Techniques with Isotope Dilution," 66 *Archives of Dis. in Childhood*, pp. 220–222 (1991).

P.S.W. Davies et al., "Body Water Measurements in Growth Disorders," 66 *Archives of Dis. in Childhood*, p. 1467 (1991).

M.B. Caldwell et al., "1994 Revised Classification system for Human Immonudeficiency Virus Infection in Children Less than 13 years of Age," 43 *Morbidity and Mortality Weekly Report* (1994).

*Primary Examiner*—Max Hindenburg
*Assistant Examiner*—Pamela L. Wingood
*Attorney, Agent, or Firm*—Baker & Botts, L.L.P.

[57] ABSTRACT

A method for predicting fat free mass (FFM) and total body water (TBW) of a prepubertal child infected with human immunodeficiency virus (HIV) comprises the steps of measuring a child's height, measuring the child's total body resistance, and predicting fat free mass (FFM) and total body weight (TBW) of said child using the measured height and total body resistance.

6 Claims, No Drawings

METHOD OF PREDICTING BODY COMPOSITION IN PREPUBERTAL CHILDREN INFECTED WITH HUMAN IMMUNODENFICIENCY VIRUS

BACKGROUND OF THE INVENTION

Growth failure and wasting are common complications of Human Immunodeficiency Virus (HIV) infection in children, contributing to the morbidity and mortality. The ability to measure body composition gain or loss in these children associated with infection is crucial to clinical study in ways to alleviate these problems. Developing precise methods for measuring body composition in order to monitor nutritional status in these children is an important area of research. Traditional methods for determining body composition have limited availability and can be difficult to perform, especially with young children.

Bioimpedance analysis (BIA), on the other hand, is inexpensive, rapid and non-invasive. To perform body composition analysis, the bioimpedance analyzer is affixed to a patient's wrist and ankle with electrodes. A current of approximately 800 microamps at 50 kHz is then delivered. Resistance (the voltage drop of the applied current) and reactance (opposition to electric current caused by capitance) are then measured in a matter of minutes. These values, along with other variables, are used to predict different body composition variables.

Due to its ease of use and portability, BIA has been demonstrated to be an attractive alternative to traditional methods for estimating total body water (TBW) and fat free mass (FFM) in children. For instance, the following predictive equations have been developed for estimating TBW using BIA where H=height, R=resistance, W=weight and Z=impedance.

Fjeld et al. developed equations for predicting TBW in well and malnourished children as:
TBW=0.48+0.68($H^2$/R), and TBW=0.76+0.18($H^2$/R)+0.39 (W). Fjeld et al., Total Body Water Measured by 0 Dilution and Bioelectric Impedance in Well and Malnourished Children, 27 *Pediatric Research* 98–02 (1990).

Danford et al. determined a predictive equation for TBW, using the tetrapolar method of BIA as:
TBW=1.84+0.45($H^2$/R)+0.11(W). Danford et al., Comparison of Two Bioelectrical Impedance Analysis Models for Total Body Water Measurement in Children, 19 *Annals of Human Biology* 603–607 (1992).

Davies et al. found that TBW results using the following equation were highly predictive:
TBW=−0.5+0.60($H^2$/R). Davies et al., The Prediction of Total Body Water Using Bioelectric Impedance in Children and Adolescents, 15 *Annals of Human Biology,* 237–240 (1987).

Gregory et al. used the following equation to predict TBW in children with growth disorders:
TBW=0.79+0.55($H^2$/Z). Gregory et al., Body Water Measurement in Growth Disorders: A Comparison of Bioelectrical Impedance and Skinfold Thickness Techniques With Isotope Dilution, 66 *Archives of Disease in Children* 220–222 (1991).

Davies and Gregory went on to find that combining their equations into one equation resulted in a more accurate predictor of TBW:
TBW=0.13+0.58($H^2$/Z). Davies and Gregory, Body Water Measurements in Growth Disorders, 66 *Archives of Diseases in Childhood* 1467 (1991).

The following predictive equations have been developed for estimating FFM. Deurenberg et al. found that several predictive equations were required to estimate FFM and that choice of the most accurate equation was dependent on the age of the children. Two of the equations are:
FFM=0.640($10^4$)($H^2$/R)+4.83, (Ages 7–9 for boys & girls)
FFM=0.488($10^4$)($H^2$/R)+0.221(W)+12.77(H)−14.7, (Ages 10–12 for girls and 10–15 for boys). Deurenberg et al., Assessment of Body Composition by Bioelectric Impedance in Children and Young Adults is Strongly Age-Dependent, 44 *European Journal of Clinical Nutrition* 261–268 (1989).

Cordain et al. evaluated BIA with children using the following equation to predict FFM:
FFM=6.86+0.81($H^2$/R). Cordain et al., Body Composition Determination in Children Using Bioelectrical Impedance, 52 *Growth, Development & Aging* 37–40 (1988).

Houtkooper et al. studied several predictive equations and recommended the following for predicting FFM:
FFM=−0.61($H^2$/R)+0.25(W)+1.31. Houtkooper et al., Bioelectrical Impedance Estimation of Fat-Free Body Mass in Children and Youth: A Cross-Validation Study, 72 *J. Anal. Physiol.* 366–73 (1992).

No studies, however, have assessed the accuracy of BIA, using standard equations, in predicting TBW and FFM in children infected with HIV.

An object of the present invention is to provide an improved method for predicting FFM and TBW in children infected with HIV which is more accurate than other known methods.

A further object of the invention is to provide a method for estimating FFM and TBW in these subjects which is clinically practical and more accommodating than other methods.

Further objects of the invention will readily appear to those skilled in the art from a review of the invention as disclosed and claimed.

SUMMARY OF THE INVENTION

In accordance with the present invention, a method for predicting fat free mass (FFM) and total body water (TBW) of a prepubertal child infected with human immunodeficiency virus (HIV) is disclosed whereby total body resistance and height are measured to predict the body composition values.

Preferably, the total body resistance is determined by performing bioimpedance analysis (BIA) on a subject using the results to calculate resistance according to previously derived formulae known in the art. A tetrapolar bioimpedance analyzer is preferred.

DETAILED DESCRIPTION

A study using 20 subjects was performed to assess the performance of bioimpedance analysis (BIA) in the prediction of total body water (TBW) and fat free mass (FFM) using standard equations in children infected with human immunodeficiency virus (HIV). The study suggests that TBW and FFM can be estimated in children with HIV using BIA with special equations specifically developed in this group of children.

Methods and Subjects

The subjects were twenty prepubertal children ages 4–11 years with HIV infection as defined by the Centers for Disease Control and Prevention (CDC) criteria. They were recruited for the study from the St. Lukes-Roosevelt Hospital Center Pediatric HIV/AIDS Program.

The characteristics of the study subjects are presented in Table 1 below. Nineteen of the subjects acquired HIV as a result of perinatal transmission and one was infected as a result of a blood transfusion while a neonate. Most of them had moderate to severe symptoms of HIV infection including moderate to severe immunodeficiency. None had known or suspected active secondary or opportunistic infections or clinically apparent cardiac or renal disease.

After an overnight fast, measurements were taken. The subjects were weighed to the nearest 0.01 kg using a beam balance. Their height was measured to the nearest 0.1 cm using a fixed wall-mounted stadiometer. Total body resistance (R) and reactance were measured with a tetra polar bioelectrical impedance analyzer manufactured by RJL Systems (RJL model 101 A, Detroit, Mich.) using bioimpedance analysis (BIA) techniques as disclosed in allowed U.S. patent application Ser. No. 08/353,933 to Kotler, now pending, filed on Dec. 12, 1994, which is incorporated herein by reference.

To assess the accuracy of the BIA, TBW was independently measured by a dilution technique with an oral dose of 0.1 gm/lb of body weight of deuterium oxide with concentration of tracer measured in saliva ($^2H_2O$ dilution). FFM was also assessed by dual energy x-ray absorptiometry (DXA) using Lunar DPX and pediatric software, v. 8e. Growth and results of lymphocyte phenotype analyses performed within 3 months of the study were obtained from each subject's medical records.

Eight published prediction equations, as disclosed above, for TBW and FFM in children, based on BIA, including two developed for children with growth disorders, which used simple, easily obtained measurements, were selected for the study. The values predicted by these prior art equations were compared to the measured values in the subjects of the present invention using the paired t test.

According to the present invention, new equations have been derived for TBW and FFM using regression techniques. The Box-Cox family of transformations was used to determine if it was necessary to transform the dependent variables and to identify the transformations. The set of independent variables considered for inclusion in the model included ($height^2$/resistance), ($height^2$/reactance), weight and age. Residual analyses were performed on the final equations. The Epinfo (USD, Inc. Stone Mountain Ga.) software package was used for calculation of the height, weight and weight for height-age-percentiles. All statistical calculations were performed using the STATA (Computing Resource Center, Santa Monica, Calif.) and SAS (SAS Institute, Inc., Cary, N.C.) software packages for personal computers. The level of significance for all statistical tests was 0.05.

Results

Table 2 presents results of the comparison of TBW and FFM predicted from the published equations referenced above with TBW measured by $^2H_2O$ dilution and FFM measured by DXA. The values predicted by each equation were significantly different from those measured (correlation coefficient (p) values ranging from 0.02 to 0.001).

Since none of the tested published equations adequately predicted TBW or FFM in the sample group of the present invention, two regression equations according to the present invention were developed for this sample as follows:

$$Log(TBW) = 1.65 + 0.05\ (H^2/R)\ (r^2=0.95, SEE=0.068)$$

and $$FFM = 1.34 + 0.70(A) + 0.68(H^2/R)\ (r^2=0.95, SEE=1.23);$$

where:
- TBW=total body water (1)
- FFM=fat free mass (kg)
- H=height (cm);
- A=age (yrs);
- R=resistance (ohms);
- $r^2$=correlation coefficient; and
- SEE=standard error estimate.

The addition of sex, weight and ($height^2$/reactance) did not significantly improve the prediction of either TBW or FFM in the study.

Discussion

These results indicate that the published standard equations established for generally predicting body composition from BIA-derived measurements in children are not valid for application to children with HIV infection. This study also indicates that highly predictive equations specific for this population using simple, standard variables can be devised. Indeed, predictive equations based on BIA-derived resistance which provide estimates of TBW and FFM comparable to those of traditional, more complex methods of body composition measurements were derived in the present invention. As a result, the new equations of the present invention provide a means for using BIA to predict body compartments (TBW or FFM) in children with moderate to severe symptoms of HIV, moderate to severe immunodeficiency, and with abnormal growth, such as those included in the study.

While the foregoing indicates the preferred embodiments of the invention claimed below, those skilled in the art will appreciate that there are variations of this disclosure which do not depart from the scope of the invention claimed herein. For example, different methods of BIA may be used in conjunction with the claimed equations such as those providing different amperages and frequencies.

TABLE 1

Characteristics of 20 HIV-infected children undergoing study.

| Variable | Mean ± SD (range) |
|---|---|
| Age (yrs) | 6.5 ± 2.3 (4–11) |
| Height (cm) | 117.4 ± 13.8 (97.9–147.5) |
| Height-for-age-percentile (%) | 35.2 ± 29.8 (0.1–93.1) |
| Weight (kg) | 23.3 ± 7.9 (14.1–44.5) |
| Weight-for-age-percentile (%) | 43.4. ± 36.6 (2.5–96.5) |
| Weight-for-height percentile (%) | 56.2 ± 36.4 (2.8–99.9) |
| Total body water (L)[a] | 13.7 ± 4.6 (8.0–25.7) |
| Fat free mass (kg)[b] | 18.4 ± 5.5 (11.6–31.0) |
| Resistance (ohms) | 785 ± 116 (543–1012) |
| $Height^2$/Resistance | 18.38 ± 5.94 |
| CD4 count (no/dl) | 319 ± 330 (4–1099) |
| CD4 percent (%) | 16.8 ± 13.8 (0.6–40.4) |
| | No. (%) |
| Race/ethnicity | |
| Black | 6 (30) |
| Hispanic | 14 (70) |
| CDC classification | |
| N3 | 1 (5) |
| A2 | 3 (15) |
| B2 | 3 (15) |
| B3 | 5 (25) |
| C1 | 2 (10) |
| C2 | 3 (15) |
| C3 | 3 (15) |

TABLE 1-continued

Characteristics of 20 HIV-infected children undergoing study.

| Variable | |
|---|---|
| Growth pattern | |
| AIDS Wasting Syndrome[c] | 2 (10) |
| Progressive stunting[d] | 9 (45) |
| Normal | 9 (45) |
| Sex | |
| males | 9 (45) |
| females | 11 (55) |

[a]Total Body water determnined by deuterium oxide dilution.
[b]Fat free mass determined by dual energy absorptiometry.
[c]Weight loss of ≧10% within 3 months of study.
[d]Decline in height-for-age-percentile of 2 or more SD (e.g. 95th, 75th, 50th, 25th, 5th percentile for age) within 2 years before, or 6 months after the time of study and without weight loss.

TABLE 2

Evaluation of BIA-based predictive equations for TBW and FFM with TBW measured by deuterium oxide dilution and FFM by dual X-ray absorptiometry in children infected with HIV.

| Study | N | Age (yrs) | Variables | Body Compartment | Predicted Weight (+SD) (kg)[1] | Predicted − Measured[2] | p |
|---|---|---|---|---|---|---|---|
| Fjeld et al. | 30 | 0.4–3 | $H^2/R,W$ | TBW | 12.95 (4.1) | .75 | .02 |
| Danford et al. | 37 | 5–9 | $H^2/R,W$ | TBW | 12.81 (3.94) | .88 | .009 |
| Davies et al. | 26 | 5–18 | $H^2/R$ | TBW | 10.61 (3.64) | 3.03 | .001 |
| Gregory et al. | 34 | 7–15 | $H^2/R$ | TBW | 11.03 (3.3) | −2.67 | .001 |
| Davies and Gregory | 60 | 5–18 | $H^2/R$ | TBW | 10.93 (3.5) | −2.77 | .001 |
| Deurenberg et al. | 827 | 7–25 | $H^2/R,G,A,W,H$ | FFM | 16.08 (4.88) | −2.28 | .001 |
| Cordain et al. | 30 | 9–14 | $H^2/R$ | FFM | 21.75 (4.82) | 3.39 | .001 |
| Houtkooper et al. | 94 | 10–14 | $H^2/R,W,X_c$ | FFM | 19.69 (4.93) | 1.33 | .001 |

[1]Values expressed as mean ± SD.
[2]TBW measured by deuterium oxide dilution (mean = 13.7 L) and FFM measured by dual X-ray absorptiometry (mean = 18.4 kg), as presented in Table 1.
TBW = total body water
FFM = fat free mass
H = height
W = weight
R = resistance
A = age
G = gender
$X_c$ = Reactance
N = number subjects studied
p = correlation coefficient

We claim:

1. A method for predicting fat free mass (FFM) and total body water (TBW) of a prepubertal child infected with human immunodeficiency virus (HIV), comprising the steps of:

measuring a height of said child;
   measuring total body resistance of said child; and
   predicting fat free mass (FFM) and total body weight (TBW) of said child using said height and said total body resistance.

2. A method for predicting fat free mass (FFM) and total body water (TBW) of a prepubertal child infected with human immunodeficiency virus (HIV), comprising the steps of:

measuring a height of said child;
   providing at least one signal representative of said height;
   measuring total body resistance of said child;
   providing at least one signal representative of said resistance; and
   predicting fat free mass (FFM) and total body weight (TBW) of said child using said signals.

3. The method of claim 2 wherein said resistance measuring step comprises the step of using a bioimpedance analyzer.

4. The method of claim 3 wherein the bioimpedance analyzer is a tetrapolar bioimpedance analyzer.

5. The method of claim 1 wherein the predicting step comprises the steps of determining fat free mass and total body water of said child, according to:

$$FFM = 1.34 + 0.70A + 0.68\ H^2/R$$

and $$Log(TBW) = 1.65 + 0.05\ H^2/R$$

where:
   FFM=fat free mass (kg)
   TBW=total body water (l)
   A=age (yrs)
   H=height (cm) and
   R=total body resistance (ohms).

6. The method of claim 2 wherein the predicting step comprises the steps of determining fat free mass and total body water of said child, according to:

$$FFM = 1.34 + 0.70A + 0.68\, H^2/R$$

and $$\mathrm{Log}(TBW) = 1.65 + 0.05\, H^2/R$$

where:
- FFM=fat free mass (kg)
- TBW=total body water (l)
- A=age (yrs)
- H=height (cm) and
- R=total body resistance (ohms).

* * * * *